United States Patent
Deykoon

(10) Patent No.: US 8,433,119 B2
(45) Date of Patent: Apr. 30, 2013

(54) EXTENSION OF THE FIELD OF VIEW OF A COMPUTED TOMOGRAPHY SYSTEM IN THE PRESENCE OF INTERFERING OBJECTS

(75) Inventor: Anton M. Deykoon, Arlington, MA (US)

(73) Assignee: Analogic Corporation, Peabody, MA (US)

( * ) Notice: Subject to any disclaimer, the term of this patent is extended or adjusted under 35 U.S.C. 154(b) by 859 days.

(21) Appl. No.: 12/605,207

(22) Filed: Oct. 23, 2009

(65) Prior Publication Data

US 2011/0096968 A1    Apr. 28, 2011

(51) Int. Cl.
 *A61B 6/03* (2006.01)
(52) U.S. Cl.
 USPC ................ 382/131; 378/15; 378/18; 378/19
(58) Field of Classification Search .................. 382/131; 378/15, 18–19
 See application file for complete search history.

(56) References Cited

U.S. PATENT DOCUMENTS

| | | | | |
|---|---|---|---|---|
| 6,810,102 | B2 * | 10/2004 | Hsieh et al. ........................ | 378/4 |
| 2005/0063507 | A1 * | 3/2005 | Baba et al. ........................ | 378/11 |
| 2007/0253523 | A1 * | 11/2007 | Zamyatin ........................... | 378/4 |

OTHER PUBLICATIONS

Jeong et al., Reduction of artifacts due to multiple metallic objects in computed tomography, Feb. 27, 2009, Medical Imaging 2009: Physics of Medical Imaging, SPIE vol. 7258, pp. 3E-1 to 3E-8.*
Zeng et al., Estimating 3-D Respiratory Motion from Orbiting Views by Tomographic Image Registration, 20076, IEEE, vol. 26, No. 2, pp. 153-163.*
Chityala et al., Artifact reduction in truncated CT using Sinogram completion, 2005, SPIE vol. 5747, pp. 2110-2117.*
Hsieh et al., "A novel reconstruction algorithm to extend the CT scan field-of-view," Med. Phys., 31:2385-2391 (2004).
Sourbelle et al., "Reconstruction from truncated projections in CT using adaptive detruncation," Eur. Radiol, 15:1008-1014 (2005).
Zamyatin, "Extension of the reconstruction field of view and truncation correction using sonogram decomposition," Med. Phys., 34:1593-1604 (2007).

* cited by examiner

*Primary Examiner* — Toan Ton
*Assistant Examiner* — John Corbett
(74) *Attorney, Agent, or Firm* — McDermott Will & Emery LLP

(57) ABSTRACT

A method and system for generating a field of view extension of a CT scan and minimizing the effect of interfering objects is described. The system is configured and the method carries out the steps of generating a full sinogram based upon CT scan data of a scanned object and any interfering objects within the scanning field; determining the location of any interfering objects within the CT data based on physical and geometrical properties of the interfering objects; generating an ideal sinogram of any interfering objects based on their location and physical properties; subtracting the ideal sinogram from the full sinogram; extending a sinogram free of any interfering objects; and adding the ideal sinogram of interfering objects to the extended sinogram of the scanned object. Speeding up the computation of the extended sinogram by creating a look-up table of the tunable parameter of the extension function.

17 Claims, 11 Drawing Sheets

US 8,433,119 B2

EXTENSION OF THE FIELD OF VIEW OF A COMPUTED TOMOGRAPHY SYSTEM IN THE PRESENCE OF INTERFERING OBJECTS

FIELD OF THE DISCLOSURE

The present disclosure relates to Computed Tomography (CT) Scanners, and more particularly, to a CT scanner and method of extending the field of view of a CT scan in the presence of interfering objects.

BACKGROUND OF THE DISCLOSURE

A $3^{rd}$ generation CT scanner has a finite measured field-of-view (hereinafter "MFOV") defined by the shortest distance from the isocenter to rays extending from the x-ray source to the edge detectors. The MFOV of a typical CT scanner is 50 cm, which is sufficient for radiology. However, when CT is combined with another modality, such as radiation therapy or PET, the patient is positioned to place the target area (typically a tumor) closer to isocenter. As a result, the limbs of the patient may be positioned outside of the MFOV of the CT subsystem. Consequently, extension of the reconstructed field-of-view (hereinafter the "RFOV") up to 60-70 cm may be needed to capture the entire cross-section of the region of the patient that is of interest.

If a part of the patient is located outside of the MFOV, the measured projections are truncated at one or both edges (the edges being defined by the two edges of the MFOV where the outmost rays extending from source to the edge detectors intersect the MFOV). Images reconstructed from truncated projections have characteristic bright artifacts which corrupt the image inside and outside of the MFOV. In order to avoid truncation artifacts and recover the anatomy outside of the MFOV, the truncated projections need to be extended beyond the MFOV.

One approach to extending truncated projections is based on parallel (rebinned) projections, where the total amount of attenuation in a view does not change with view index. If at least one non-truncated projection is available, then the total attenuation of each view is known, so that the total attenuation in the extension for each truncated view may be computed.

If a view is truncated on both edges, the missing attenuation needs to be distributed between the left extension and the right extension. If the position of the center-of-mass (COM) of the patient is known, the missing attenuation in the doubly truncated projection is distributed such that the center of mass of the extended parallel projection agrees with the COM.

At least one known extension technique is optimized for anatomical objects. However, truncation may also be caused by non-anatomical interfering objects, such as (a) reinforced edges of the pallet of the patient table; (b) restraining equipment; (c) equipment for intravenous injections. Interfering objects generally increase the total amount of truncation and reduce the quality of the extension. Thus a method and system for extending truncated projections in the presence of interfering objects is needed.

One technique for extending the RFOV in fan projection space is described in U.S. Patent Application Publication 2007/0076933 (Starman et al.). The advantages of the algorithm described in the Starman et al. application are improved accuracy of CT numbers in the extended region(s), better stability under various truncation scenarios, and better extension when a large portion of anatomy is truncated. However, at least two disadvantages of the algorithm described in the reference are longer development time and slower speed.

SUMMARY OF THE DISCLOSURE

According to one aspect of the disclosed system and method the RFOV of a CT scanner is extended in the presence or absence of interfering objects. Interfering objects (IO) are objects which reside fully or partially outside of the MFOV and whose properties and positions are known. IO's generate extra truncated views in addition to the truncated views due to the patient. The extension of truncated views in presence of IOs is of lower quality than extension of views truncated only by the patient.

In accordance with one embodiment the quality of extension is improved through (a) predicting the sinogram of any IOs, (b) subtracting the sinogram from the original sinogram of both the scanned object (such as a patient) and any IOs, extending the remaining scanned object sinogram, and (c) adding the subtracted sinogram of IO back to the extended sinogram.

The process and improved system are particularly useful when a CT machine is combined with a device that is operable in a different modality, such as a PET scanner, or as a part of a radiation therapy machine.

GENERAL DESCRIPTION OF THE DRAWINGS

DETAILED DESCRIPTION OF THE DRAWINGS

For illustrative purposes the disclosed process and improved system are illustrated as a part of a radiation therapy machine.

In general, a high energy radiotherapy machine combines a CT X-ray imaging system for providing the functionality of a simulator in order to map select regions of a scanned object for follow up radiation treatment therapy, and high energy radiotherapy for delivering therapeutic radiation to the select regions. An example of such a machine is shown and described in U.S. Pat. No. 6,914,959 to Bailey et al. (incorporated herein by reference), assigned to the present assignee, and illustrated by way of example in FIGS. 1 and 2. In the illustrated embodiment the X-ray imaging system can be used for both planning treatment and subsequently used during treatment. The X-ray imaging system is preferably a high resolution imaging system that can create images using CT reconstruction techniques, as well as stationary and scout views. Preferably, the stationary and scout views can be stereoscopic views for determining the position of the target region relative to and/or within a region of interest.

Figure 1:
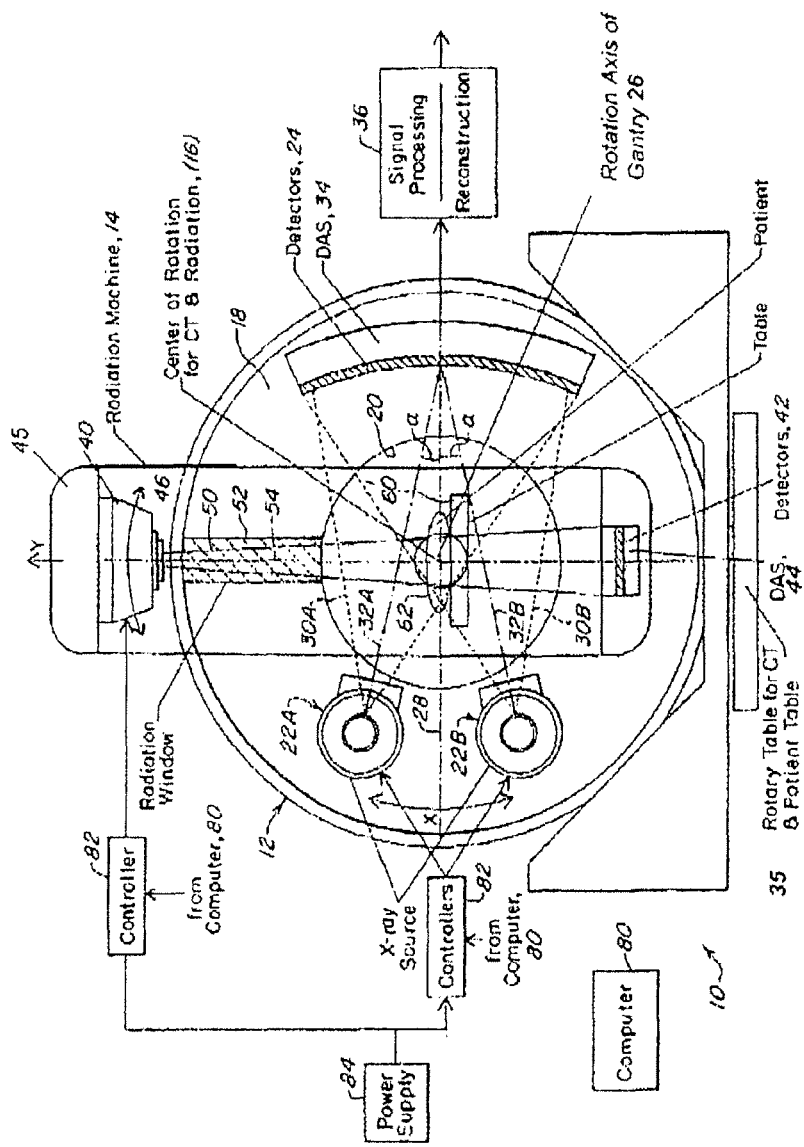
FIG. 1 illustrates a front view of an embodiment of a radiation therapy machine.
Figure 2:
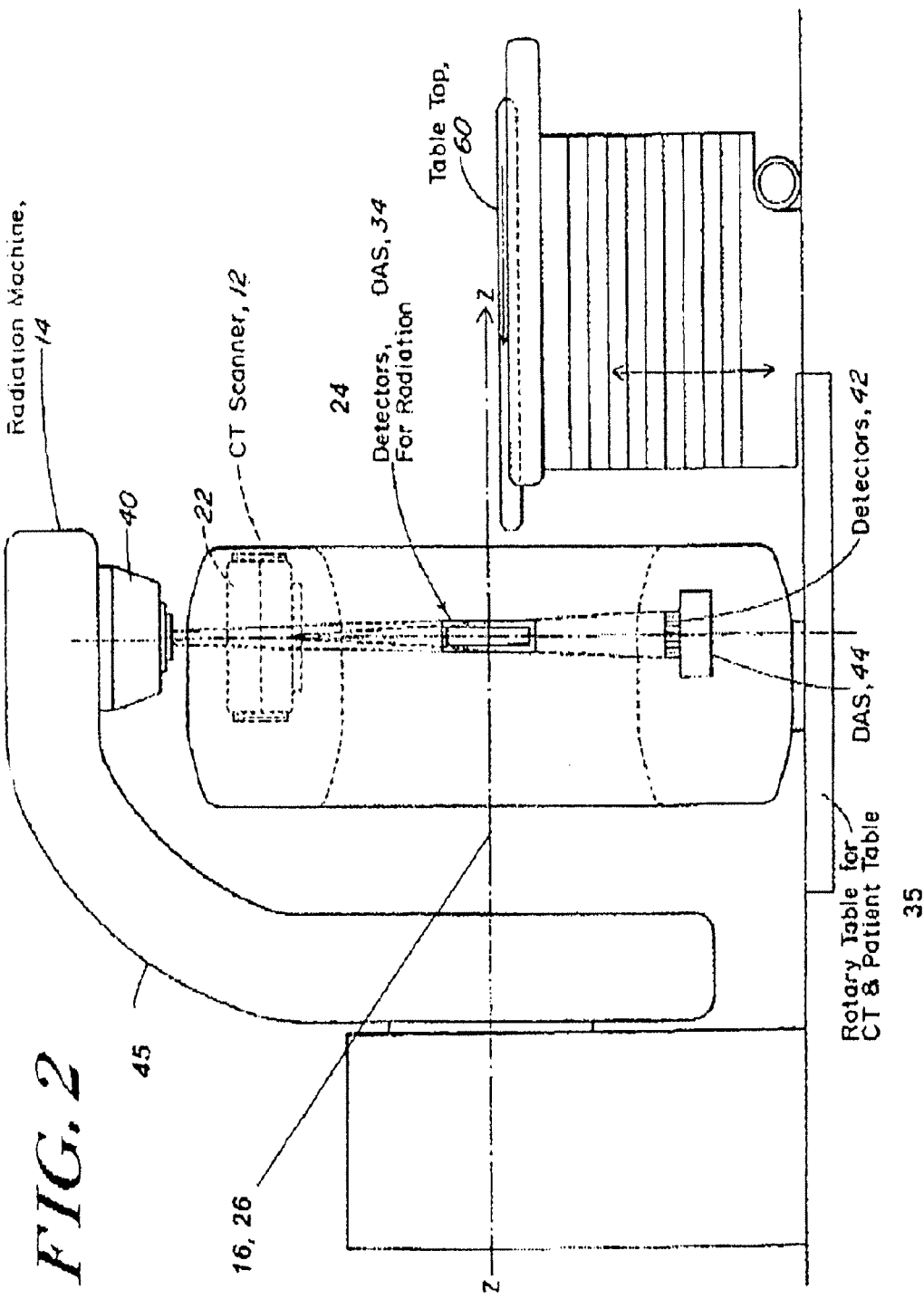
FIG. 2 illustrates a side view of the embodiment of the radiation therapy machine illustrated in FIG. 1.

Referring to FIGS. 1 and 2, the radiation therapy machine 10 includes CT imaging subsystem 12, and the therapy radiation subsystem 14 mounted for rotation about the same isocenter 16.

The imaging system 12 includes a rotatable gantry 18 having a patient aperture 20. A pair of X-ray sources 22A and 22B (or moving electron beam source) and a detector array 24 are fixedly mounted on the gantry 18 to rotate with the gantry around the isocenter 16 about a rotation axis 26 (defining a z-axis seen in FIG. 2). The sources 22 are positioned almost diametrically opposite the detector array 24 on opposite sides of a bisector 28 passing through the isocenter 16 and the geometric center of the array 24 such that an imaging x-ray fan beam 30A (or 30B) of each source is emitted from the source toward the detector array 24 along a center line 32A (or 32B), displaced by an angle α relative to a bisector 28. In addition, the sources 22 can be fixed relative to the detector array 24 such that the imaging x-ray fan beams 30A and 30B are shifted ¼ of the detector pitch. In FIG. 2, the x-ray source 22 is shown in broken lines simply to illustrate that it is movable with the gantry 18. The x-ray source 22 and the detector array 24 are normally located diametrically across from one another on the gantry 18.

The detector array 24 includes one or more rows of detectors suitably connected to a data acquisition system (DAS) 34, which in turn is connected to suitable components used in CT scanners (indicated at 36) so as to form image data of one or more slices respectively through one or more slice planes passing through at least a portion of the patient's body positioned in the patient aperture 20 within a region of interest, referred to as the field of view (FOV), and as mentioned above the MFOV In addition, the radiotherapy subsystem 14 is preferably positioned to pivot about the same Z-axis and isocenter 16. The therapy radiation subsystem 14 includes a high energy X-ray source 40 and one or more high energy detectors 42. As shown the source 40 is mounted on a pivotal support such as a C-arm 44, while the high energy detectors 42 are mounted on the gantry 18. Alternatively, the high energy detectors 42 can be spatially fixed with respect to the source 40 so as to be positioned diametrically opposite the source 40 at all times. The output of the detectors 42 can be provided to a separate data acquisition system (DAS) 44. A suitable collimator subsystem (including for example, one or more known multi-leaf collimators) is provided at 46 so that the cross-sectional shape and size of the radiotherapy beam used to expose the target region of the patient can be modified depending upon the cross-sectional size and shape of the target region at the angle of the exposure by the source 40. The source 40 and detectors 42 are preferably, although not necessarily, mounted so that when the detectors 42 are positioned diametrically opposite the source 40 (relative to the isocenter) the center axis of the high energy radiotherapy beam 50 emitted from the source 40 toward the detectors 42 is aligned with (i.e., the center axis 54 of the beam 50 is contained within) a region of interest (the latter defining a radiation window 52) within the slice plane of the imaging system 12. Thus, the axis 54 of the beam 50 preferably lies within the slice plane.

Although not shown, the support 44, and thus the source 40 (with a suitable collimator), of radiotherapy subsystem 14 can be made to be pivotal about a substantially horizontal axis (indicated as the X-axis in FIG. 1) passing through the isocenter 16 preferably, although not necessarily, through at least 180 degrees. This allows the radiation window 52 to also pivot. Alternatively, the detectors 42 can be secured to the same support as the source 40 so that the two always remain diametrically opposed to one another about the isocenter 16 of the machine, and pivot together about the X-axis of the machine. In this case the detectors 42 are mounted so as to be clear the gantry.

Finally, a table 60 is provided for supporting the patient 62. The table 60 is adapted to move in the Z-axis direction (shown in FIG. 2) as well as the Y direction, i.e., up and down, and preferably also the X direction, i.e., left and right as shown in FIG. 1, all within the region of interest in the slice plane.

The imaging subsystem 12 can be used in the planning stage using standard CT techniques by positioning the patient on table 60 in the aperture 20 with the target region position close to the isocenter 16. When using the imaging system one or both of the X-ray sources 22A and 22B can be used. With one source 22 the chosen source is used to emit the X-ray beam 30 toward the detector array 24 as the source and array rotate about the rotation axis 26. Similarly, both X-ray sources can be used to acquire CT data. In this latter case, the X-ray sources can share the detectors of the array 24 by being alternatively switched so that when one X-ray source is emitting X-rays, the other is not. By switching back and fourth at a high rate, the amount of data provided by the detector array from each source can be utilized.

A computer 80 has a display screen and user entry devices (typically a keyboard and mouse), not explicitly shown in FIGS. 1 and 2. Computer is suitably connected to the radiotherapy machine 10 to control motion of the table 60 and to coordinate operation of the various moving parts, and to collect data from the detector array 24 during a scan of the patient. The machine is typically used to map a region of the body with a CT scan, and delivery MeV beam therapy to select parts of the imaged region with the radiation source 40 and its collimator.

Other radiation therapy systems are known, such as shown in U.S. Pat. Nos. 5,099,505; 5,537,452; 5,851,182; 6,289,403 and 6,385,286.

The following description, for purposes of illustration only, and not by way of limitation, assumes that the CT scanner described is a subsystem for use with such a radiation delivery machine, and the reason for extending the field of view (hereinafter the "FOV") is to create more accurate maps for beam therapy, although there may be other reasons to extend the FOV. It also assumes for purpose of illustration that a portion of the patient and/or equipment remain outside the MFOV during the scan.

One embodiment of the process of extending the MFOV will now be described. In the illustrated embodiment, the RFOV is created based on parallel projections in each tilted slice of a volumetric scan. In the illustrated reconstruction process, the extension step is placed after tangential interpolation and before radial interpolation. Each truncated projection is extended with a smooth monotonous curve. The curve is constrained by the value and derivative of the truncated projection at the truncation point and by the total area under the curve.

A property of parallel projections that helps to predict the size of the extension is defined as follows: Let $P_{par}[k,q]$ represent parallel axial projections of a discrete view index k and continuous detector coordinate q. Let $P_{sum}[k]$ be integral of a parallel projection over the detector coordinate and defined as follows:

$$P_{sum}[k] = \int_{-\infty}^{+\infty} P_{par}[k,q]dq \quad (1)$$

The disclosed embodiment takes advantage of the following property of parallel projections: the integral of parallel projections does not depend on the view index k:

$$P_{sum}[k] = I_0, \text{ for all } k \quad (2)$$

where $I_0$ is a constant.

Measured parallel projections, $P_{par}^m[k, s]$, have a discrete coordinate s, which does not extend to $\pm\infty$. For measured parallel projections, Eq. (2) is true only in non-truncated views. In truncated views the integral of parallel projections will be less than $I_0$. In order to prevent the artifact caused by truncation, parallel views need to be extended. In each extended view, the area under the extension should compensate for the difference between $I_0$ and the area under the measured projection.

The conservation of parallel projections can be used to extend the FOV of a scanner in helical mode. In helical mode the data may be reconstructed using method described in Larson, et al "Nutating slice CT image reconstruction apparatus and method," U.S. Pat. No. 5,802,134 hereinafter referred to a Nutated Slice Reconstruction or "NSR". The key element of NSR is interpolation of helical data into tilted planes which are chosen to minimize the difference between the tilted data and an axial data acquired through the same plane. The tilted data is subsequently interpolated from fan to parallel (but not equi-spaced) projections. These projections are called hybrid projections. Interpolation of hybrid projections in the detector direction generates equi-spaced parallel projections which may be reconstructed using any one of several well-known filtered backprojection methods.

The disclosed technique extends the FOV of the hybrid projections using conservation of the integral of parallel axial projections. The conservation is perturbed by two errors. The first error is due to hybrid projections being an approximation of parallel axial projections through the tilted plane. The second source of error is physical imperfections of the data caused by beam hardening effects, photon starvation, scatter, and other view-dependent effects. Standard corrections are made for the physical imperfections before the application of NSR.

Figure 3:
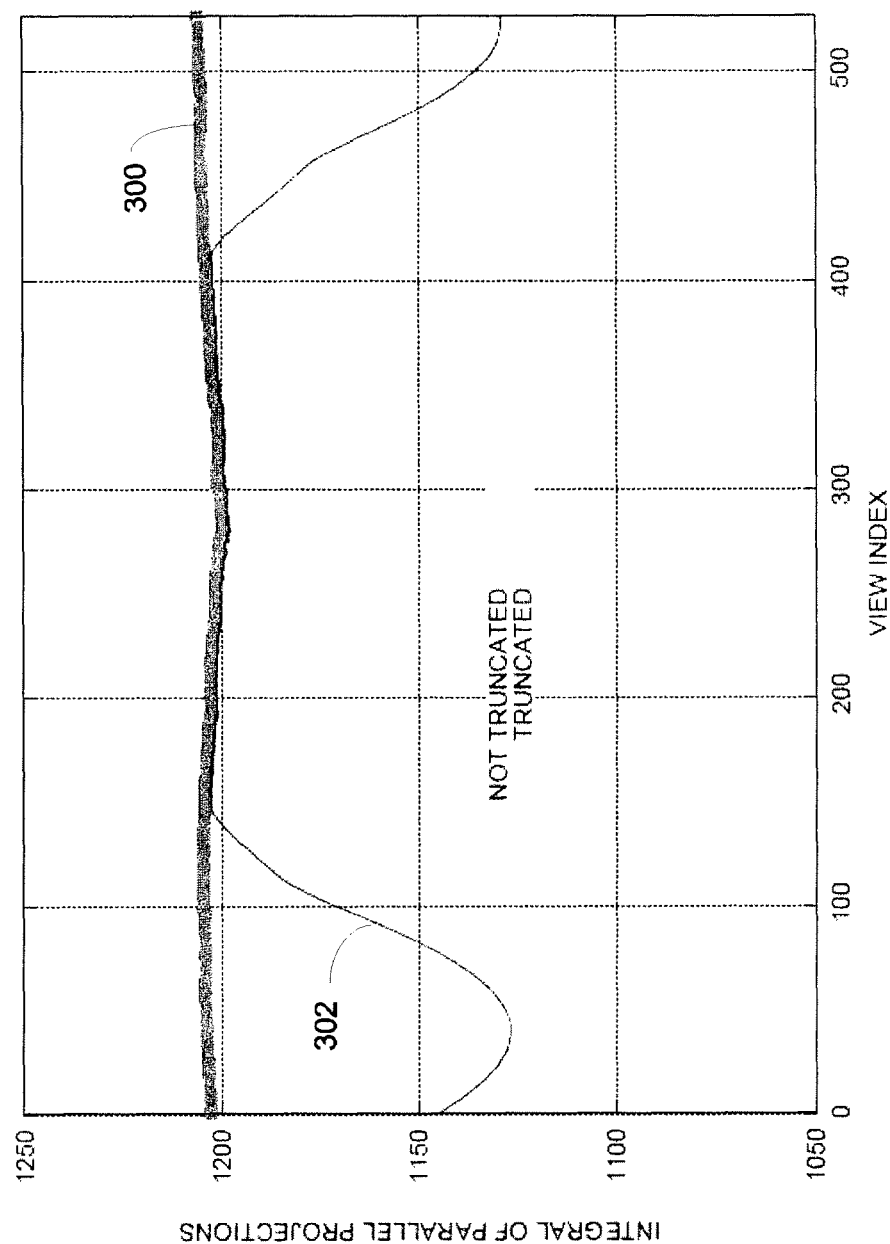
FIG. 3 is a graphical illustration of two curves respectively illustrating the measured integral of non-truncated and truncated hybrid parallel projections in a tilted slice as a function of view.

Measured integral of non-truncated hybrid parallel projections in a tilted slice as a function of view is shown by way of example as curve 300 in FIG. 3. The data belongs to a helical scan of an Alderson anatomical torso phantom. The phantom is scanned entirely inside of the measured FOV, i.e., variability of the integral of measured projections is due to the factors other than truncation. A shoulder section of the phantom is scanned to maximize the beam hardening and photon starvation effects. The peak-to-peak variation of the measured integral is 0.8%. The projections are subsequently truncated by setting the first 100 samples in each view to zero. By comparison the integral of truncated projections is shown by curve 302 in FIG. 3. One can see that the deficiency of the integral due to truncation exceeds in most of the truncated views the variability due to other factors.

In practice, the value of $I_0$ is approximated as a maximum of the integral of measured parallel projections over all views:

$$I_0 = \max_{k_h=1}^{N_{v\_tan}-1} P_{sum}^m[k_h] \quad (3)$$

where $N_{v\text{-}tan}$ is the number of parallel views per rotation.

The deficiency in the integral of parallel projection, called missing area, may be estimated as:

$$E_{err}[k_h] = I_0 - P_{sum}^m[k_h] \quad (4)$$

The concept of the missing area will be used as a requirement to an extension function which is described as follows.

Consider an extended hybrid view $P_{hyb}[k_h, s]$, where $k_h$ is the view index and $0 \leq s < N_{det\_fath}$ is the detector index and $N_{det\_fath}$ is the number of samples in extended view. The measured data is a subset of the extended set $N_{fi} \leq s \leq N_{hf}$, where $N_{fi}$ and $N_{hf}$ are the indexes of the first and the last measured samples in the extended view.

Figure 4:
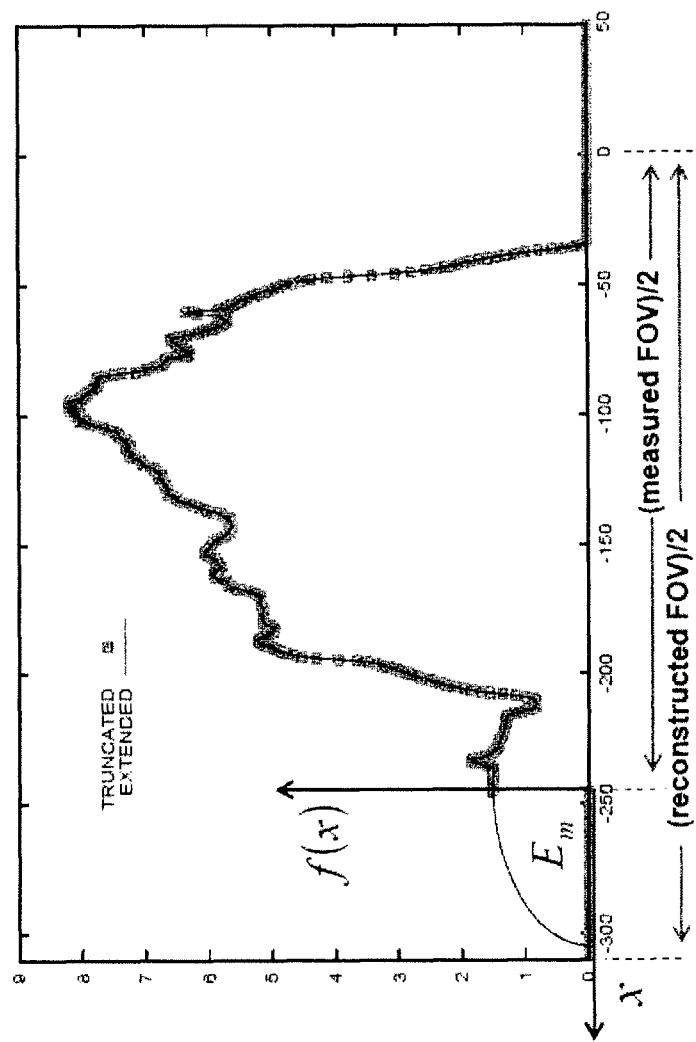
FIG. 4 is a graphical illustration showing an example of a left extension wherein x is the extension coordinate and f(x) is the extension function, for a truncated and extended MFOV/2 and a RFOV/2.

Consider a view $k_h$ which is truncated on the left side: $P_{hyb}[k_h, N_{fi}] > 0$, $P_{hyb}[k_h, N_{hf}] = 0$. An example of left extension is shown in FIG. 4, wherein x is the extension coordinate, f (x) is the extension function. The sample index in extended region is defined as $0 \leq s \leq N_{fi}$. The coordinate of the extended sample runs from x=0 at $s=N_{fi}-1$ away from the center as shown in FIG. 4.

The extension function f (x) is expected to satisfy the following requirements:

1. The value of projection is continuous at the truncation point:

$$f(x)|_{x=0} = P_{hyb}[k_h, s]|_{s=N_{fi}} \quad (5)$$

2. The derivative of projection is continuous across the truncation point:

$$\left.\frac{df(x)}{dx}\right|_{x=0} = \left.\frac{dP_{hyb}[k_h, s]}{ds}\right|_{s=N_{fi}} \quad (6)$$

3. The area under the extension matches the missing area:

$$\int_0^\infty f(x)dx = E_{err}[k_h] \quad (7)$$

In software implementation, the integral will be approximated by a sum. In a view which is truncated on both sides, the sum of areas under the left and right extension must match the missing area.

4. The extension is positive. A corollary of this requirement is that the range of non-trivial values of extension are limited to the interval $0 \leq x < x_{max}$ where $x_{max}$ is the smallest positive root of f(x)=0.

5. The extension reaches its minimum value at the last point of the extension, $x_{max}$.

The following extension function is used:

$$f(x) = \sqrt{Ax^2 + Bx + C} \quad (8)$$

Similar functions are known and can be used that are based on extending parallel projections. Zero order coefficient, C, and first order coefficient, B, are responsible for matching projection value and derivative at truncation point, respectively. Second order coefficient, A, is introduced to satisfy the missing area requirement. Increasing the value of A makes the extension longer without affecting the value or derivative at the truncation point.

The first step 502 is to identify the truncated cases. A truncation "case" specifies an index of a truncated view and the truncated side (left or right). Next, at step 504 the integral of projections is computed in each view. The missing area is identified at step 506 in each view. At step 508, the zero order and first order coefficients of extension function are computed based on the value and the derivative of the projection at the truncation point. If a view is truncated on both sides, the missing area is distributed between left and right extension as noted at step 510. The second order coefficient of extension function is then determined at 512 to satisfy the missing area requirement. Next, the extension function f(x) is computed in the extended region at step 514. Area under extension is computed at step 516. If area under extension deviates from the missing area, replace parabolic form of f(x) with a linear ramp at step 518. Finally, at step 520 extension samples are set to f(x) for points satisfying $f(x)>0$, $0 \leq x < x_{max}$.

Figure 5:
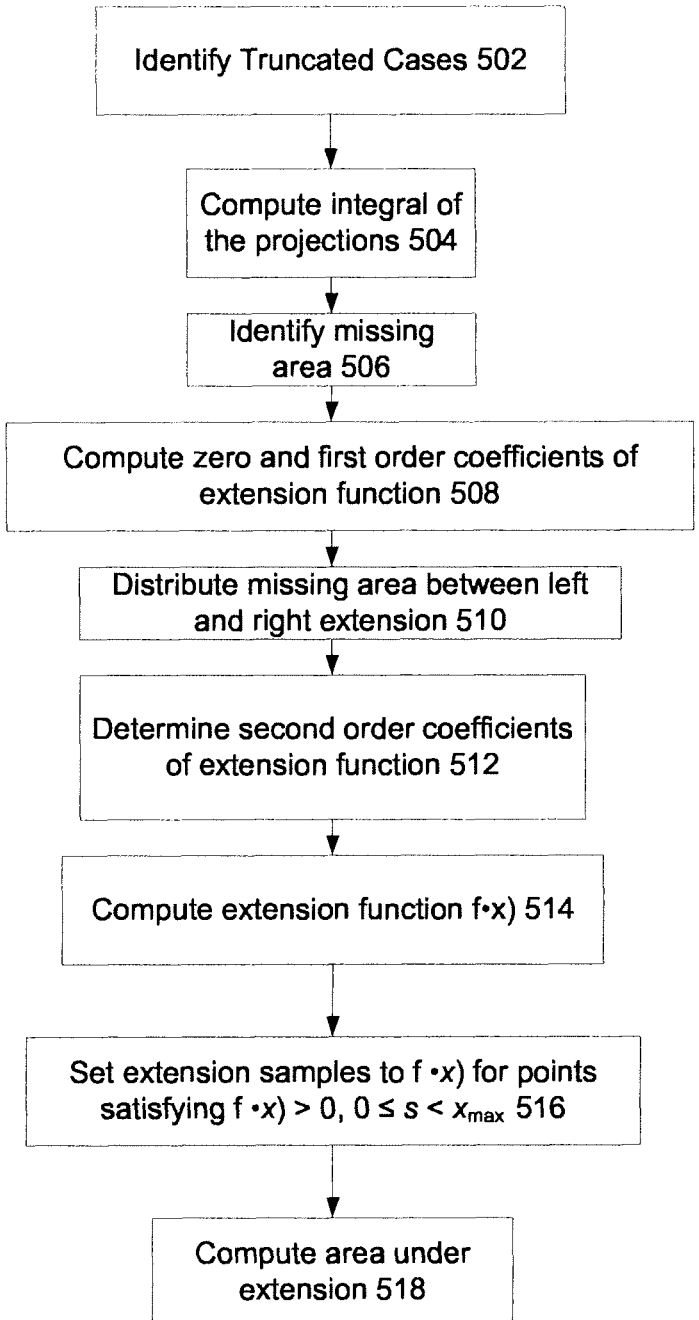
FIG. 5 is a flow chart illustrating an embodiment of the disclosed extension technique.

Detailed description of the steps of the embodiment illustrated in FIG. 5:

Step 502. Identify truncation cases $T(k_h,i)$ where $k_h$ is the view index, and $i=0, 1$ is the index for distinguishing the left and the right side of the projection. If the projection value on the left side of a measured view $k_h$ exceeds a pre-determined threshold, $T(k_h,0)$ is set to 1. Similarly, if the projection value on the right side of a measured view exceeds the threshold, flag vector $T(k_h,1)$ is set to 1.

Step 504. The integral of the parallel projections is computed for each view using a trapezoid rule of integration for discretely sampled data. The trapezoid integration takes into account varying spacing between samples in the hybrid data.

Step 506. The missing area for each view is computed according to Eq. (4).

Step 508. Coefficients B and C are computed as follows:

$$C(k_h,i) = P(k_h,i)^2 \quad (9)$$

$$B(k_h,i) = S(k_h,i)P(k_h,i) \quad (10)$$

where $S(k_h,i)$ is the slope of projection at the truncation point.

Step 510. The missing area is then distributed. If a view is truncated on both ends (doubly truncated), the missing area $E_{err}[k_h]$ is distributed between the left and right ends of the view as $wE_{err}[k_h]$ and $(1-w)Eerr[k_h]$, respectively. w is the distribution weight:

$$w[k_h] = \frac{(P_{hyb}[k_h, N_{hf}])^3}{(P_{hyb}[k_h, N_{hfh}])^3 + (P_{hyb}[k_h, N_{fh}])^3} \quad (11)$$

An alternative approach to distributing the missing area is based on the conservation of the center of mass (COM), as described, for example, in K. Sourbelle, M. Kachelriess, W. A. Kalender "Reconstruction from truncated projections in CT using adaptive detruncation," Eur. Radiol. (2005) 15: 1008-1014. The alternative approach is based on predicting the position of the COM of a doubly truncated view through the COMs in the non-truncated views. Then the missing area in the doubly truncated view is distributed between left and right extensions such that the COM of the extended view matches the prediction. This approach is useful when the fraction of truncated views is below 40%. As the fraction of truncated views increases, the accuracy of predicting the position of the COM in a doubly truncated view falls, leading to unacceptable errors in distributing the missing area. The patient table for radiation therapy is typically bigger than the patient table for diagnostic CT, resulting in an increased fraction of truncated views due to the table. Thus the approach given by Eq. (11), which depends only on the projection values in the current view, is more desirable for a robust FOV extension.

Step 512. The second order coefficient of the extension function f(x) needs to be determined based on coefficients B, C and the value of missing area $E_{err}$. Analytical integration of f(x) from $x=0$ to $x_{max}$ yields a transcendental equation involving A, B, C, and $E_{err}$. The equation may not be solved for A analytically. In order to speed-up and stabilize the finding of A, the extension uses a three-dimensional look-up table. The table is addressed through three look-up indexes which are generated from the values of B, C, and $E_{err}$. The procedure for finding A through a look-up table contains pre-computation step 2 which is done once per scanner model. Steps 1 and 3 are performed once per reconstruction, while steps 4 and 5 are performed at runtime per-case. Steps 1-5 are described below:

1. Generate vectors $t_B[\ ]$, $t_C[\ ]$, and $t_E[\ ]$ representing discrete grids for B, C, and $E_{err}$, respectively.

2. For each combination of indexes $i_B$, $i_C$, and $i_E$, compute and record into a look-up table the value of A which satisfies requirements of Eq. (8). This step is a pre-computation which removes tuning of A for each combination of B, C, and $E_{err}$ from online implementation. In some cases all requirements may not be satisfied. For example, large negative values of B call for short extensions, whereas large values of E require long extensions. The missing area requirement is given up first, i.e, the last value of A which satisfied requirements for B and C with a lower value of $E_{err}$ is recorded into the look-up table. This rule prevents values of A which result in unphysical extensions. Running the index $i_E$ as in internal loop is recommended, starting from the lowest value of $E_{err}$. If and when the missing area requirement is not satisfied for the first time at index $i_E^0$, the value of A corresponding to the same $i_B$, $i_C$, and $i_E = i_E^0 - 1$ may be copied into the remaining nodes of the look-up table along the E-axis: $i_E^0 < i_E < N_E$.

3. The look-up table is then loaded on the reconstruction computer during a preparation stage.

4. For each truncation case, values of B, C, and $E_{err}$ are mapped into indexes $i_B$, $i_C$, and $i_E$. The indexes point to the nearest smaller values of appropriate vectors:

$$t_B[i_B] \leq B < t_B[i_B+1]$$

$$t_C[i_C] \leq C < t_C[i_C+1]$$

$$t_E[i_E] \leq E_{err} < t_E[i_E+1] \quad (11)$$

5. The value of A is estimated using bilinear interpolation of eight values of A from the look-up table. The values are looked-up from vertices of a 3D rectangular box which contains the point (B, C, $E_{err}$).

Step 518. The elliptical extension function described above is then optimized for extending the truncation of a uniform material. During the testing of the elliptical extension, examples were encountered where the truncated region contained both bone and soft tissue, e.g., the truncation of an arm. Projections where bone contributes to the measured attenuation at truncation point have a steep slope which forces a shortened extension and generation of a bright truncation artifact. The artifact is prevented by replacing the shortened elliptical extension with a longer ramp extension. Since a steep slope at the truncation point may be legitimate, e.g., high-density object on the boundary of measured FOV, the ramp extension is applied if the mismatch of the area under extension and the missing area exceed a pre-determined threshold.

Figure 6:
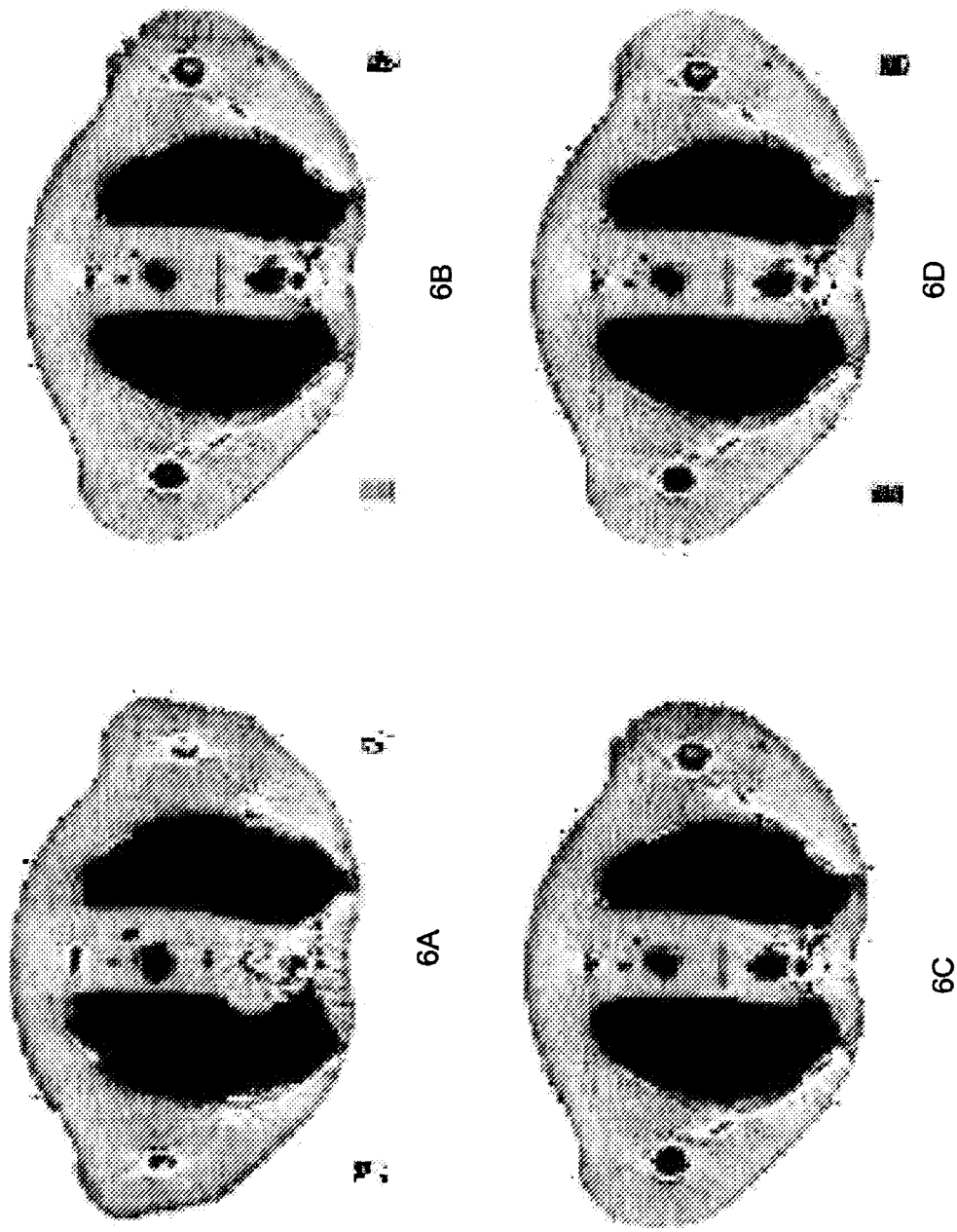
FIG. 6 is a series of reconstructed images of an anatomical phantom using the IO subtraction technique described herein.

Another type of object which may cause artifact in RFOV is IO, i.e., non-anatomical object whose properties may be known. What follows is the description of subtraction of IO for improving the quality of images in RFOV. For purposes of description, and not limitation, FIG. 6 illustrates an example of images of an anatomical phantom scanned in the presence of IOs. The term sinogram as described with reference to FIG. 6 means a two-dimensional data set representing attenuation measured by a CT scanner. The first dimension of the sinogram is related to the detector index of the scanner and called "sample". The second dimension of the sinogram is called "view". View index is proportional to the angle of the gantry as it rotates around the object being scanned. In the following discussion "parallel sinogram" or "rebinned sinogram" are considered where all samples in one view represent parallel rays passing through the object. Not truncated views of a parallel sinogram have the same sum of samples, which is proportional to the mass of the object in the scanned cross-section.

FIG. 6A shows a reconstructed image of a truncated sinogram extended with a linear ramp which matches value but does not match the slope and sum of the extended values. The truncation of the object on the left side and especially on the right side of the image in FIG. 6A is visible. Referring to FIG. 6B, the parabolic extension of a full parallel sinogram, which is a sum of the sinogram of anatomy and the sinogram of IOs. The IOs interfere with the extension. The interference results in the dark line artifact on the right side of the image.

In FIG. 6C the illustrated image is the result of reconstruction after subtracting the sinogram of the IOs from the full sinogram. Finally, with regard to FIG. 6D, the idealized sinogram of the IOs is added to the extended sinogram of the anatomy. It should be evident that the image of the right 10 is improved.

Figure 7:
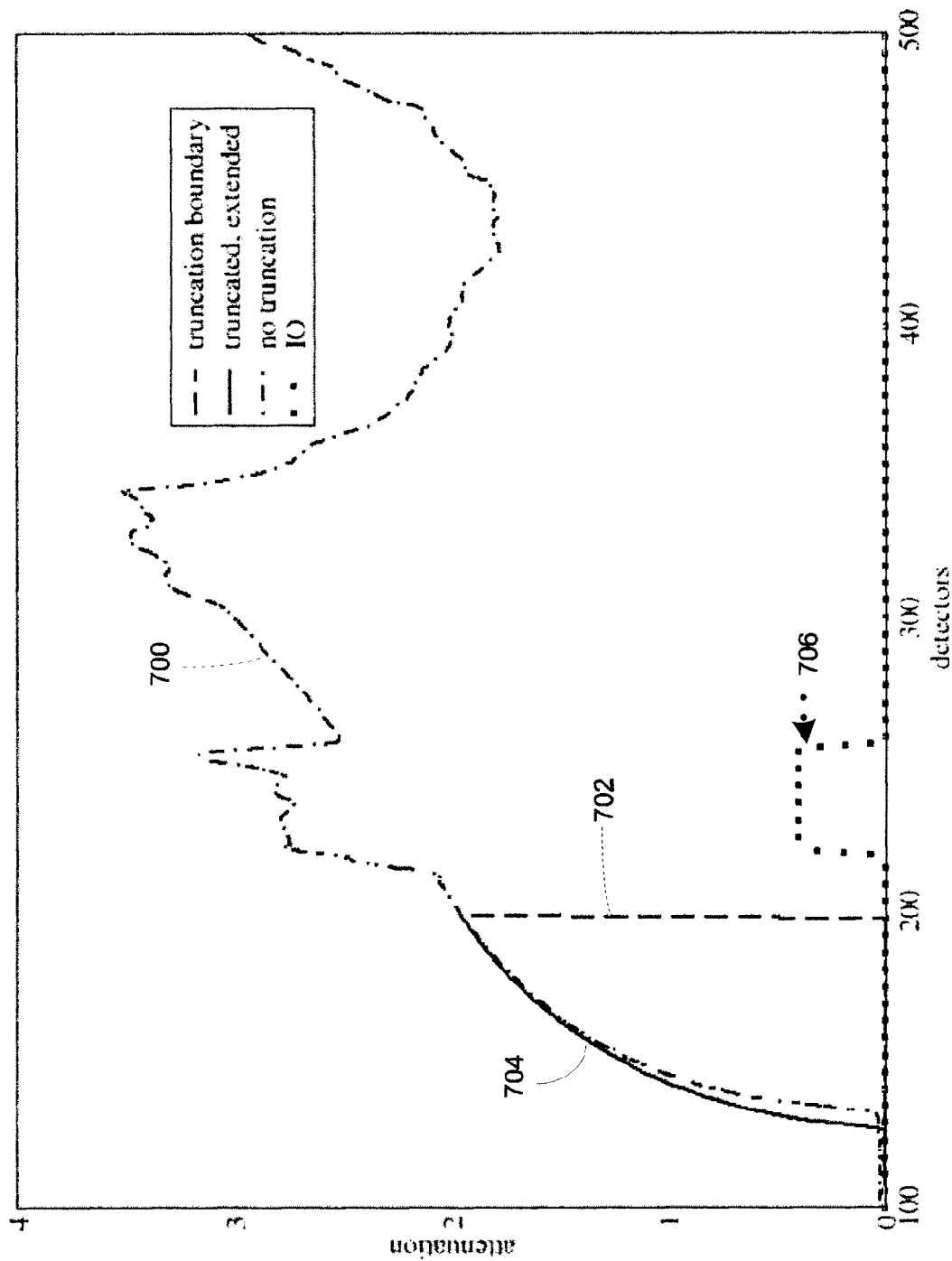
FIG. 7 is graphical illustration showing the extension of a truncated view where IO does not interfere with the extension.

FIG. 7 is a graphical illustration showing the extension of a truncated view where 10 does not interfere with the extension. Not truncated data is shown with stippled line 700. The first measured sample corresponding to detector 200, is indicated by the vertical line 702. The extension runs from sample corresponding to detector 200 to sample corresponding to detector 130, as shown by the solid line 704. One can see that the extension closely matches the not truncated projection. The dotted line 706 shows the same view if only 10 were scanned. One can see that 10 is entirely inside the measured FOV.

Figure 8:
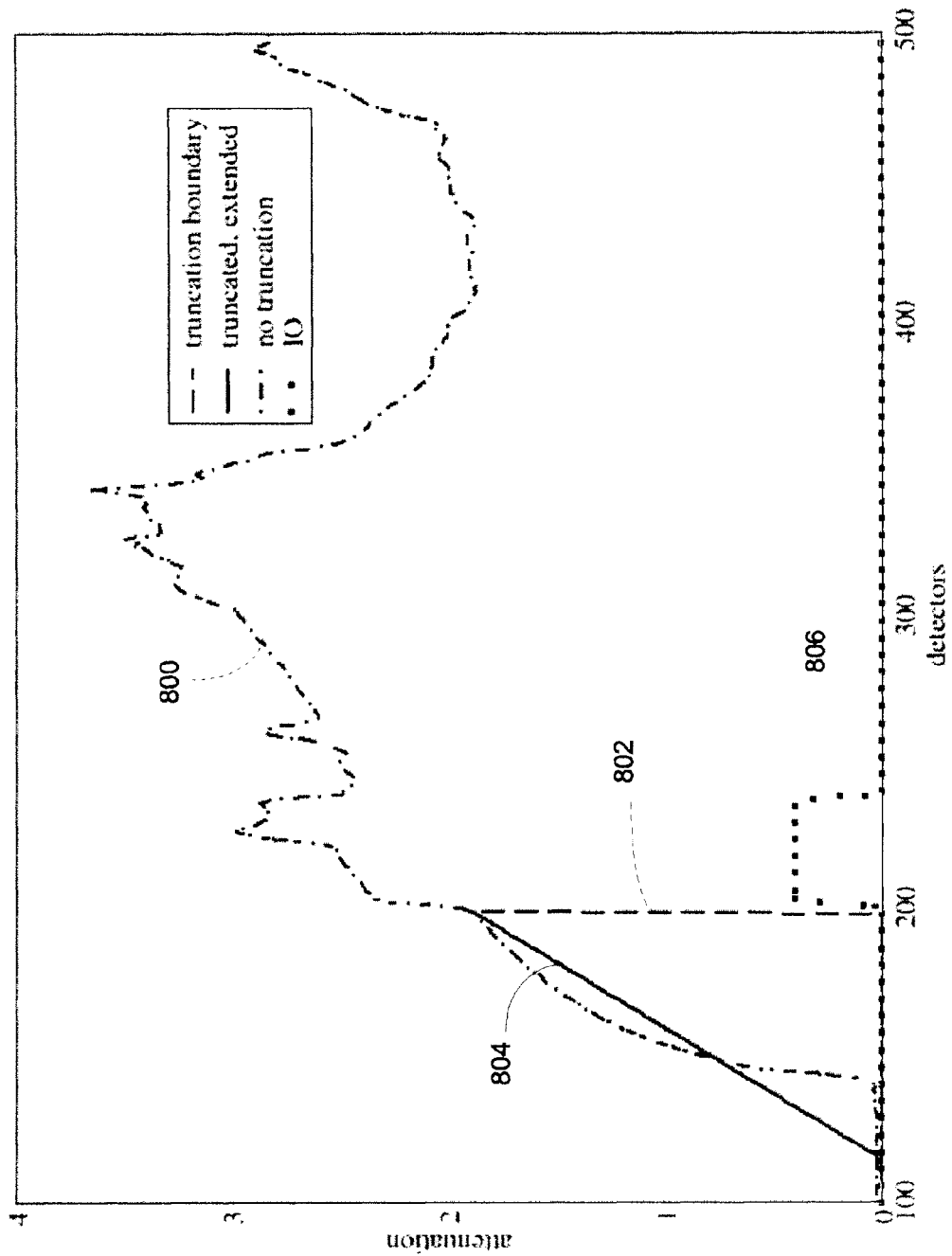
FIG. 8 is graphical illustration showing the extension of a truncated view where IO does interfere with the extension.

FIG. 8 is a graphical illustration showing the extension of a truncated view where the 10 interferes with the extension. In this event, not truncated data is shown with stippled line 800. The first measured sample received by detector 200, is indicated by the vertical line 802. The extension runs to the left of vertical line 802 in the illustration, from sample corresponding to detector 200 to the sample corresponding to detector 130, as shown by the solid line 804. The extension does not match not truncated data. The dotted line 806 shows the same view if only IO were scanned. One can see that the left boundary of IO is aligned with the truncation point. The 10 disrupts the extension by modifying the slope of the view near the truncation point.

Figure 9:
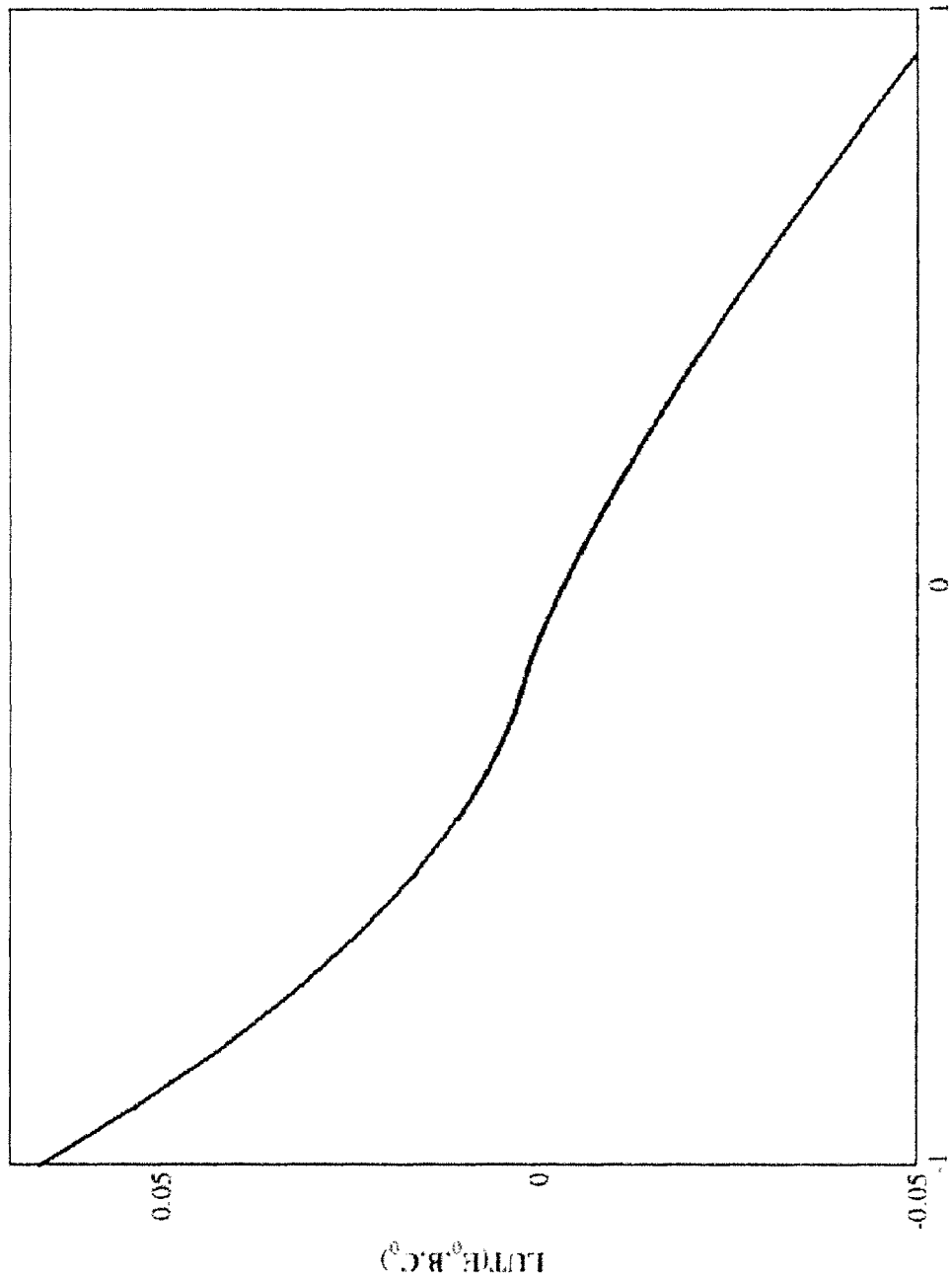
FIGS. 9, 10 and 11 are exemplary plots of values of the look-up table for the second-order coefficient of FOV extension function.
Figure 10:
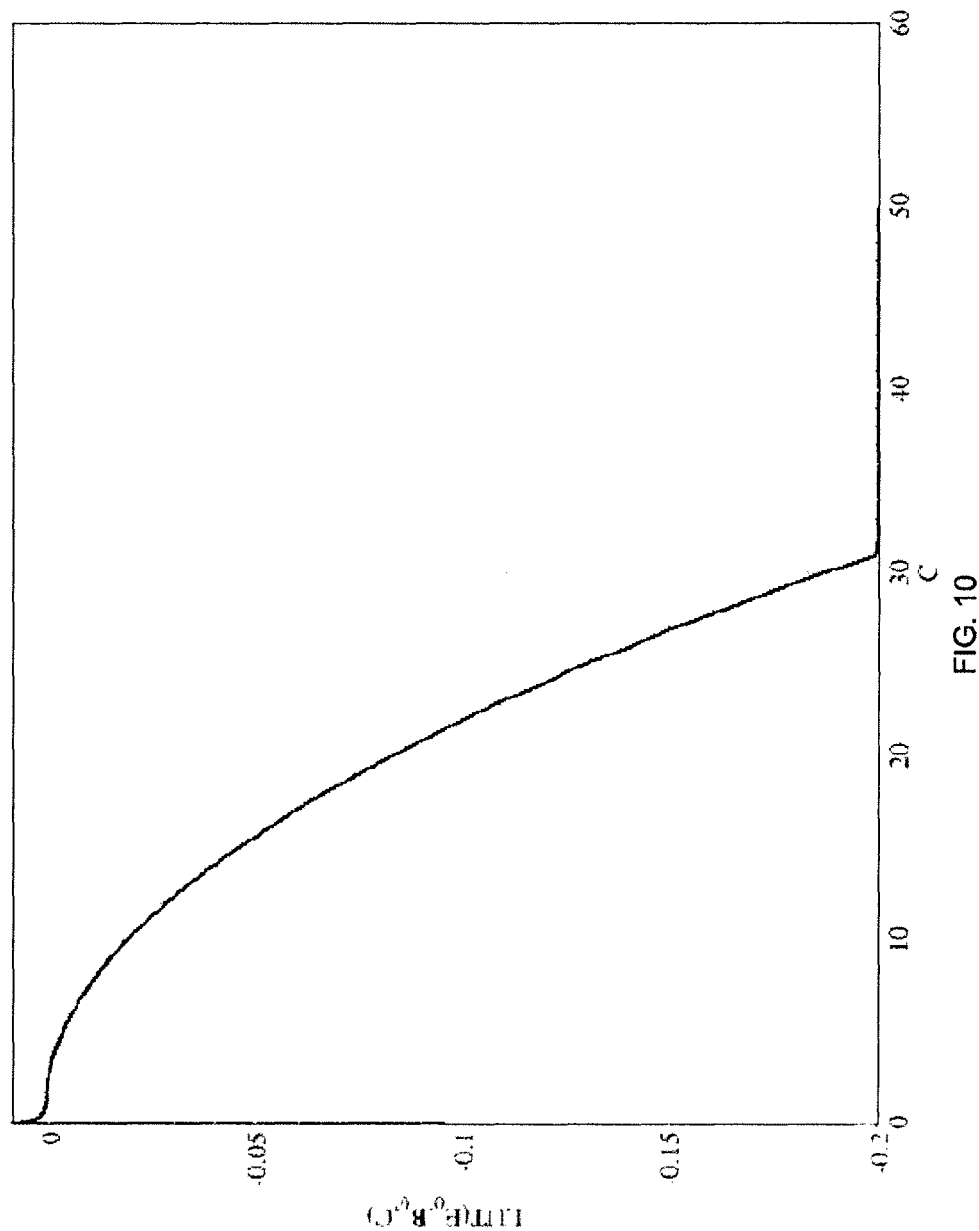
Figure 11:
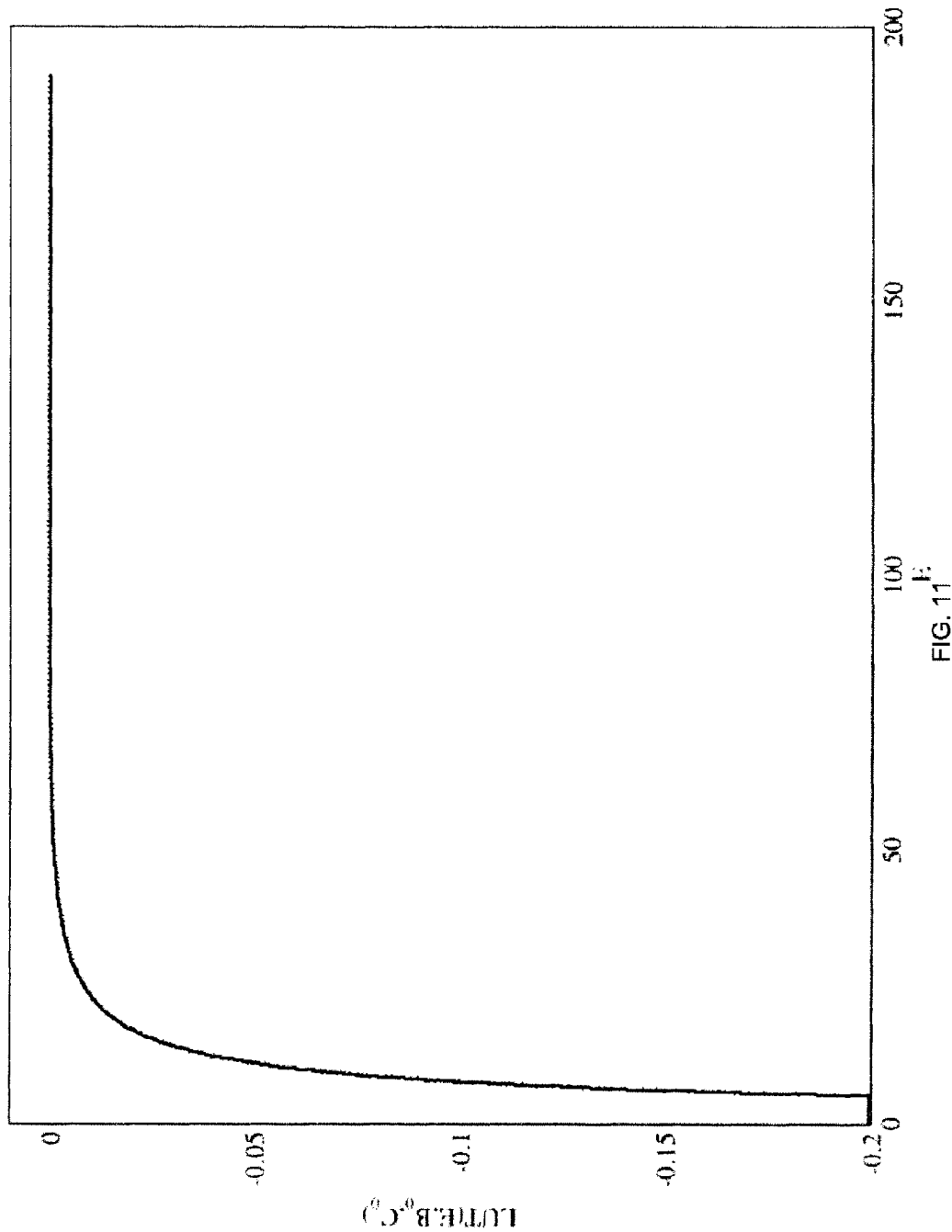

As mentioned above, for each combination of indexes $i_B$, $i_C$, and $i_E$, the value of A which satisfies the requirements of Eq. (8) is computed and recorded into a look-up table. This step is a pre-computation which removes tuning of A for each combination of B, C, and $E_{err}$ from online implementation. FIGS. 9, 10 and 11 are exemplary plots of values of the look-up table for the second-order coefficient of FOV extension function. The plots clarify how the look-up table is built, paying attention to the stability of the extension with respect to the input parameters.

The look-up table, LUT(E,B,C), is driven by three parameters derived from the parallel view being extended:
E is the predicted sum of values in the extension;
B is proportional to the slope of projection at the truncation point; and
C is the square of the value of projection at the truncation point.

Typical values of LUT are negative, which ensures that extension function, computed as $$f(X) = \sqrt{C + BX + LUT(E,B,C)X^2} \qquad (12)$$

is decreasing as X increases.

X is the local coordinate in extension. X is bounded $0 \leq X < X_{max}$, where $X_{max}$ is the length of extension. The value of X is zero at the truncation point.

FIG. 9 illustrates an example of the look-up table values as a function of parameter B. FIG. 10 illustrates an example of the look-up table values as a function of parameter C. In the example shown, the look-up table is clipped to a fixed negative number (−0.2) for values of C above 31 in order to limit the rate of decline of extension. Unbounded decline of extension may generate bright artifact similar to the artifact due to not extended views, known as "truncation artifact". Finally, FIG. 11 illustrates an example of the look-up table values as a function of the parameter E. In the example shown, the values of the look-up table are saturated at a small negative number for E>60. This limit is imposed by the requirement that extension function f(X) remains monotonous for all acceptable values of X and reaches zero before $X_{max}$. In the range 5<E<50, LUT decreases with decreasing E to match the sum of samples in the extension to E. For E<5, the LUT is set to the −0.2 to limit the rate of decline of f(X) as discussed above.

While this disclosure has been particularly shown and described with references to preferred embodiments thereof, it will be understood by those skilled in the art that various changes in form and details may be made therein without departing from the spirit and scope of the disclosure as defined by the following claims.

What is claimed is:

1. A method of generating a field of view extension of a CT scan and minimizing the effect of interfering objects, comprising:
    generating a full sinogram based upon CT scan data of a scanned object and any interfering objects within the scanning field;
    determining the location of any interfering objects within the CT data based on physical and geometrical properties of the interfering objects;
    generating an ideal sinogram of any interfering objects based on their location and physical properties;
    subtracting the ideal sinogram from the full sinogram;
    extending a sinogram free of any interfering objects; and
    adding the ideal sinogram of interfering objects to the extended sinogram of the scanned object.

2. A method according to claim 1, further including exposing the scanned object to therapeutic radiation.

3. A method of generating a field of view extension of a CT scan as a function of the input values, comprising:
    computing a second order coefficient of the field of view extension on a density grid of input values as a function of scanner geometry and forming a look-up table based thereon;

storing the look-up table in a file;
loading the file before a scan;
using the look-up table during reconstruction so as to pre-tune the second-order coefficient of the extension.

4. A method of claim 3, wherein using the look-up table provides a faster generation of the field of view extension than iterative tuning of the second order coefficient of the extension.

5. A method according to claim 3, comprising:
extending the truncated view in accordance with an elliptical function.

6. A method according to claim 5, wherein the elliptical function is in the form of $f(X)=(AX^2+BX+C)^{\{1/2\}}$,
wherein X is the local coordinate in the extension, with X=0 at the truncation point,
B and C are parameters chosen to preserve the value and slope of a CT projection at the truncation point, and
A is a parameter tuned to ensure that the area under the extension curve is substantially equal to the missing area.

7. A method according to claim 5, further including generating a sinogram of an object and any interfering objects within a truncated field of view of a CT scanner, wherein extending the truncated view in accordance with an elliptical function includes generating an interference-free sinogram in which data representing the interfering objects have been removed, and extending the interference-free sinogram.

8. A method according to claim 7, wherein data representing any interfering object in the extended view including the data that was removed is added back to make a full extended sinogram of both the scanned object and any interfering objects, so as to insure that any interfering objects are present in the final reconstructed image.

9. A method according to claim 5, wherein the elliptical function is in the form of $f(X)=(AX^2+BX+C)^{\{1/2\}}$,
wherein B and C of the extension function f(X) are parameters defined by a CT projection; and
A is a parameter that needs to be tuned.

10. A method according to claim 9, wherein the value of A is retrieved from a table of A(iE,iB,iC) using bilinear interpolation so as to shorten the time to perform the step of extending the truncated view, wherein the look-up table is pre-computed on a rectangular grid of discreet values of area, iE, slope, iB, and projection value, iC.

11. A method according to claim 10, wherein the table is stored on the reconstruction computer and loaded into reconstruction engine prior to taking a scan.

12. A method according to claim 5, further including extending the CT truncated view by distributing missing area between left and right extensions in doubly truncated views, the step of extending includes dividing the missing area E between the left and right extension based on the projection values at truncation points, $Y_L$ and $Y_R$ according to the following:

$E_L=EY_L^3/(Y_L^3+Y_R^3)$, for the left extension, and $E_R=EY_R^3/(Y_L^3+Y_R^3)$ for the right extension.

13. A method according to claim 3, further including exposing the scanned object to therapeutic radiation.

14. A system including CT scanner comprising a system for extending a truncated reconstructed field-of-view (FOV) of the CT scanner to an extended reconstructed FOV while accounting for the presence of any interfering objects, wherein the CT scanner has a measured FOV and interfering objects are objects which reside fully or partially outside of the measured FOV but within an extended FOV corresponding to the extended reconstructed FOV and whose properties and positions are known, the CT scanner comprising:
a processor for acquiring data from the scanner of a scanned object of interest and any interfering objects disposed within the measured FOV, and processing the data from the scanner including predicting a sinogram of any part of interfering objects within the extended measured FOV, subtracting the sinogram from the original sinogram of the scanned object of interest and any interfering objects within the measured FOV, extending the remaining sinogram in order to provide an extended sinogram of the patient for the extended FOV, and adding a sinogram of any interfering objects back into the extended sinogram.

15. The system of claim 14, wherein the processor is configured and arranged so as to extend the sinogram of any interfering objects extracted from the original sinogram of the scanned object and any interfering objects within the measured field of view using information known a-priori about the interfering objects so as to create an extended sinogram of any interfering object for the extended FOV prior to adding the extended sinogram of any interfering object back into the extended sinogram of the scanned object.

16. The system of claim 14, further including a source of therapeutic radiation.

17. The system of claim 16, wherein the CT scanner and source of therapeutic radiation are positioned with respect to one another so that the CT scanner maps the region of therapeutic treatment, and the source of therapeutic radiation provides therapeutic radiation to the mapped region.

* * * * *